United States Patent [19]

Hickey

[11] 4,233,978
[45] Nov. 18, 1980

[54] EXTERNAL FEMALE CATHETER

[76] Inventor: Glen A. Hickey, 706 Wesley, Glen Burnie, Md. 21061

[21] Appl. No.: 948,822

[22] Filed: Oct. 5, 1978

Related U.S. Application Data

[63] Continuation-in-part of Ser. No. 787,549, Apr. 14, 1977, abandoned.

[51] Int. Cl.³ .............................................. A61F 5/44
[52] U.S. Cl. ..................................... 128/295; 4/144.3
[58] Field of Search ............... 128/294, 295, 283, 284; 4/144.3

[56] References Cited

U.S. PATENT DOCUMENTS

| | | | |
|---|---|---|---|
| 660,388 | 10/1900 | Moberg et al. | 128/295 |
| 3,116,734 | 1/1964 | Tevman | 128/295 |
| 3,340,876 | 9/1967 | Hill | 128/295 |
| 3,373,745 | 3/1968 | Benfield et al. | 128/283 |
| 3,401,697 | 9/1968 | Lefley et al. | 128/295 |
| 3,918,433 | 11/1975 | Fuisz | 128/295 |

FOREIGN PATENT DOCUMENTS 2416036 4/1975 Fed. Rep. of Germany .......... 128/295

*Primary Examiner*—Robert W. Michell
*Assistant Examiner*—J. L. Kruter
*Attorney, Agent, or Firm*—Walter G. Finch

[57] ABSTRACT

The invention is an improved female catheter that is applied and used externally. It is particularly useful for the incontinent patient. The external female catheter is an extremely thin-walled device that is of substantially flat configuration that completely covers the entire vulva area of the female. The extremely thin walls expand easily and readily for temporary surges of expelled urine that increase the volume, but the thin walls return to the substantially flat configuration as the urine is drained out of the device. The device is reinforced at the edges by a thickening of the thin walls. The device is attached to the patient with an adhesive. Once attached to the female, it can remain in place for a considerable period of time and is capable of being flushed for sanitary purposes without removing it. The device is fitted with a drainage system to carry off expelled urine to a container attached to the leg.

5 Claims, 5 Drawing Figures

EXTERNAL FEMALE CATHETER

This is a continuation in part of U.S. Pat. Application Ser. No. 787,549, now abandoned, filed by the Applicant on Apr. 14, 1977, for an "External Female Catheter."

BACKGROUND AND SUMMARY OF THE INVENTION

The invention relates to the various means used for patients that cannot hold their urine and expel it uncontrollably. Over the years external catheters have been developed for male patients, this has not been a problem. For the incontinent female patient no satisfactory workable external catheter has been developed and placed on the market and this invention of a thin-walled, substantially flat catheter, overcomes that deficiency. Previously, indwelling catheters were used for females with a high percentage of the cases developing infection. Other types in the prior art, though termed "flexible", were of the more of less molded or cup-type that were not designed to expand and contract and were not of the flat-like configuration.

The thin-walled device of this invention uses adhesives to attach it to the body of the female and seal it against leakage. A drainage system attached to the external catheter drains expelled urine into a container attached to the leg. The container can be emptied from time to time as necessary.

The external female catheter of this invention is of a substantially flat and shallow configuration, surrounding and covering over the entire vulva area of the female and, as aforementioned, is attached with adhesives that seal it against leakage. The device is reinforced at the edges by a thickening of the material of the thin walls.

As it can be worn for a period of time (several days) if desired, it can be flushed out for sanitary purposes without removing it. Clean water or other medically prescribed solutions may be used for flushing it. The flushing is done through the connection where the aforementioned drainage system attaches to the external female catheter. A syringe may be used for this flushing process.

The adhesive used for attaching the external female catheter to the body is standard medical adhesive that does not cause irritation to the skin. Standard medical adhesive remover is used when the invented catheter is to be removed.

The material used in the external female catheter is a rubber-like material, such as a latex, that has a capability of easily expanding and stretching. If during the voiding of urine the quantity exceeds the capacity of the drainage system to carry it off as voided, the extremely thin walls of the external female catheter will stretch temporarily to a larger size until the drainage system carries off a portion of the urine. The thickened reinforced edges, which are, where the adhesive is attached, do not stretch like the thin wall portion and do not pull loose as the main portion expands.

The external female catheter is reusable and will last for a patient for a period of time with good care during its use.

It is therefore an object of the invention to provide an external catheter for females, particularly incontinent patients.

It is another object of the invention to provide an external catheter for females that can be adhesively attached to the body and easily removed.

It is still another object of the invention to provide an external catheter for females that can remain in place for an extended period of time without the need for constant removal.

It is yet another object of the invention to provide an external female catheter that can be flushed clean for sanitary purposes while still in place on the female.

It is a further object of the invention to provide an external female catheter that is stretchable and expandable to accommodate variations in the flow of urine and the speed of drainage during the time when urine is being expelled.

Further objects and advantages of the invention will become more apparent in light of the following description of the preferred embodiments.

DESCRIPTION OF THE PREFERRED EMBODIMENTS

Figure 1:
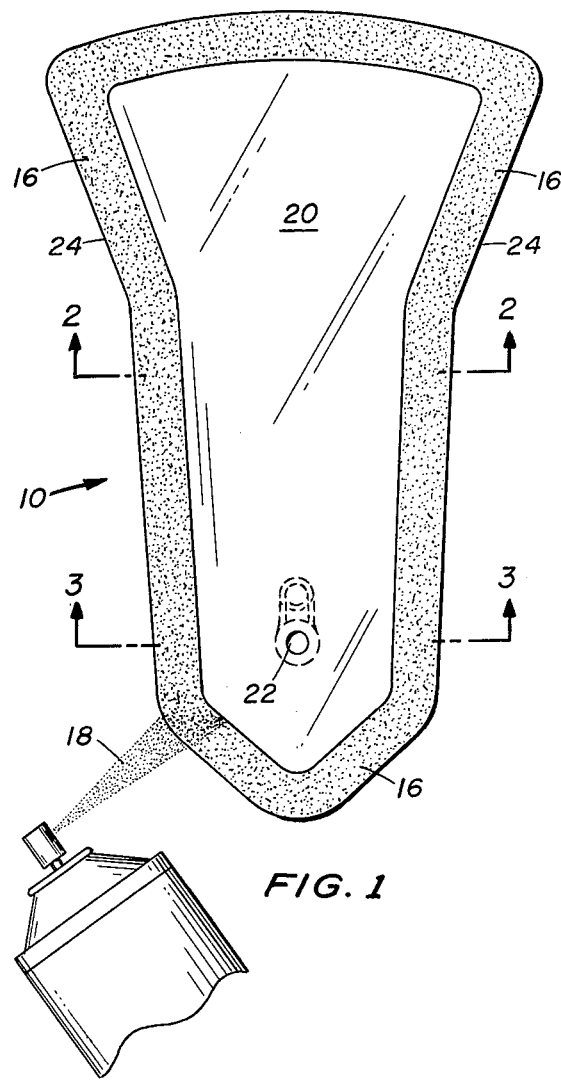
FIG. 1 is an underside view of the external female catheter, showing the adhesive surfaces.
Figure 4:
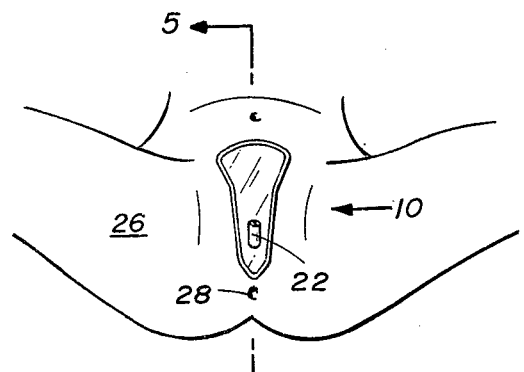
FIG. 4 is a pictorial view showing the external female catheter applied to a female patient.

Referring to the drawings and particularly to FIGS. 1 and 4, an external female catheter is shown at 10.

Figure 5:
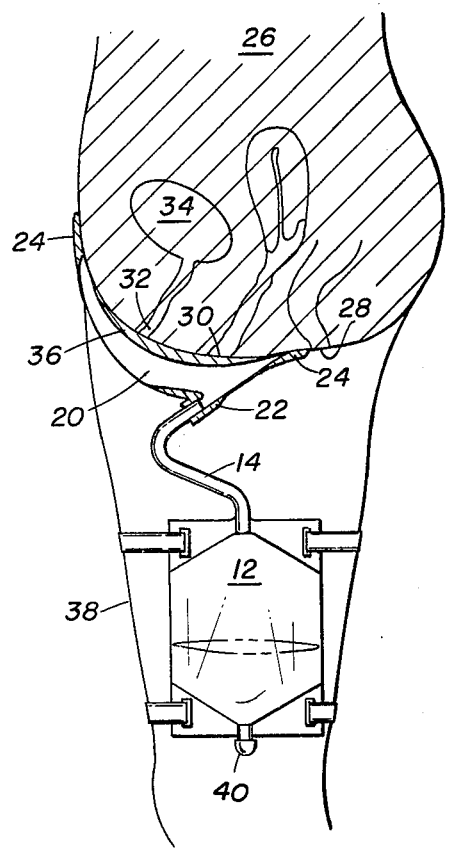
FIG. 5 is a section taken on line 5—5 of FIG. 4 and showing the urine container strapped to the patient's leg.

Referring now to FIG. 1 and the external female catheter 10, the configuration shown is such that it will completely surround and cover the area around the female patient's vulva 36, as seen in FIG. 5.

Note the configuration, in FIGS. 1 and 4, which provides for completely surrounding and covering the area around the female patient's vulva 36 (FIG. 5), but also provides a shape for an initial volume of urine and at the wide area at the top, or upper portion, for expansion for temporary surges of urine that exceed the drainage rate at the bottom or lower portion. The catheter is of one-piece construction.

The configuration is wider at the top than at the bottom, somewhat like an elongated thickened "T" shape. The top is slightly curved in an arc. The sides slope or taper inwardly toward the bottom. Near the top, the sides slope outwardly sharply to meet the curved top edge, this provides extra area and volume at the top and provides for easy expansion of the wider expanse of thin-walled rubber-like material when surges of urine require extra volume. At the bottom where the drain connection 22 is located the tapered sides are joined together in a rounded point. The device is substantially flat in configuration.

Around the edges of the external female catheter 10 in FIG. 1, the shaded areas 16 are the adhesive on the body-side surfaces with the adhesive 18 applied by manually operated spray or by aerosol methods. It should be noted that the adhesive surface 16 surrounds the entire external female catheter 10 at it's peripheral edges. It is to be understood that application of the adhesive 18 by other methods is within the scope and intent of this invention. The adhesive 18 is applied over a width at the edges 16 that is essentially the width of the reinforced edge 24 (the thickened portion) as hereinafter described.

In the external female catheter 10 in FIG. 1 the liquid containing area 20 is the entire area inside the adhesive surfaces 16. The shape of the edges of the area, which is concentric with the outer edges of the device, has been described hereinbefore. It is within this liquid containing area 20 that the expelled urine is collected prior to discharge through the drainage system hereinafter described.

Figure 2:
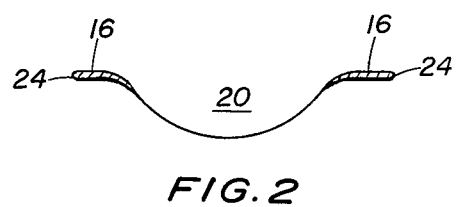
FIG. 2 is a section taken on line 2—2 of FIG. 1.
Figure 3:
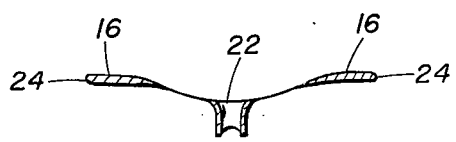
FIG. 3 is a section taken on line 3—3 of FIG. 1.

The material of the external female catheter 10 is made of an extremely thin-walled stretchable and expandable rubberlike materal, such as latex, and has substantially flat reinforced edges 24 around the entire external female catheter 10 as shown in FIG. 1. The material stretches and expands easily under very light pressure. The reinforced edge 24 is also shown in FIGS. 2, 3, and 5 and is a thickening of the material around the device at all edges. The use of an insertion of another material in the edges for reinforcement is within the scope and intent of this invention but it is to be noted that the use of a thickening of the material provides for a flexibility while the liquid containing area 20 expands.

As the female patient begins to expel urine and the liquid containing area 20 begins to fill with urine, the urine flows out of the liquid containing area 20 through the drain connection 22 at the lower narrow end. The liquid containing area 20 can be seen in FIGS. 1, 2, and 5. The drain connection 22 is shown in FIGS. 1, 3, 4, and 5. The drain connection may be monolithic with the catheter wall or may be fabricated to it.

As the liquid containing area 20 fills with urine it begins to drain through the drain connection 22. However, if a temporary rate of expelling urine exceeds the drain rate and the liquid containing area 20 completely fills while urine continues to be expelled, the extremely thin-walled aforementioned stretchable and expandable material of which the external female catheter 10 is constructed, will stretch and expand to give a temporary greater volume to receive the excessive urine. Most of this expansion will occur in the wide upper portion of the aforementioned thickened "T" shape. The continuing process through the drain connection 22 will carry off all of the urine expelled and the extremely thin-walled stretchable and expandable material of the external female catheter 10 will contract and return to its original substantially flat configuration.

Turning now to the draining process shown in FIG. 5, a drain hose 14 for transporting urine is removably connected to the drain connection 22. As shown in FIG. 5, the drain hose 14 is inserted inside the drain connection 22, however, a drain hose 14 with an inside diameter large enough to make the connection on the outside of the drain connection 22 is not precluded by this invention and is within the scope and intent of the invention.

The drain hose 14 is removably connected to a receiving bag assembly 12 to receive and store the urine that is expelled and drained from the liquid containing area 20 of the external female catheter 10. The receiving bag assembly 12 is strapped to the female patient's leg 38 so that the patient can move around while the external female catheter and the standard receiving bag assembly 12 is in place.

A drain plug 40 is part of the receiving bag assembly 12 for periodically emptying the accumulated contents. It should be noted that a receiving bag assembly 12 designed without a drain plug that is periodically emptied by disconnecting from the external female catheter 10 is not precluded. Such a variation or other minor differences in a receiving bag assembly 12 for use with the invented external female catheter is within the scope and intent of this invention.

The external female catheter 10 may be flushed while in place on the female patient. The manner of flushing may be understood by observing FIG. 5. To flush the liquid containing area 20 with clear clean water or a medically prescribed solution, the drain hose 14 is disconnected from the drain connection 22 and the clear clean water or the medically prescribed solution is injected by a syringe through the drain connection 22. If the syringe is connected directly to the drain connection 22, or connected to the drain connection 22 by a hose, the drainage of the flushing liquid can be drained back into the syringe.

Alternatives to draining back into the syringe are many and in no way preclude the intent of the invention for an external female catheter. Some such alternatives are: after inserting the flushing liquid by syringe, permit the drainage to be made into a bed pan or into a toilet if the patient can use the facility while the flushing liquid is inserted; or instead of disconnecting the drain hose 14 at the drain connection 22, disconnect the drain hose 14 at the receiving bag assembly 12 and insert the flushing liquid by syringe through the drain hose 14, with the drainage being collected from the drain hose 14 into a suitable receptacle or into a toilet.

The position of the external female catheter 10 on a female patient 26 may be seen in FIG. 4, note that the external female catheter 10 is clear of the anus 28 of the female patient 26. Thus, the external female catheter 10 does not interfere with the other necessary functions of the body.

In FIG. 5 the extent to which the area around the vulva 36 of the female patient 26 is covered can be seen clearly. Again, it can be seen that the anus 28 is clear of the reinforced edge 24 of the external female catheter 10. In completely surrounding and covering the vulva 36 of the female patient 26, both the vagina 30 and the uretha 32 are enclosed inside the liquid containing area 20. As can be seen, urine from the bladder 34 of an incontinent female patient 26, flowing down the uretha 32 will be received inside the liquid containing area 20 for the aforementioned process of ultimately draining it away from the female patient 26.

It should be noted that use of various other materials, various modifications in the configuration, and other similar modifications and variations to which the invention is susceptible, may be practiced without departing from the scope, intent, and teaching of the appended claims.

What is claimed is:

1. A female catheter (as recited in claim 4, wherein) for external application, comprising:
a receiving means, said receiving means being substantially flat and elongated in configuration, said receiving means receiving and containing a liquid, said receiving means being constructed from an extremely thin-walled stretchable and expandable material, said thin-walled stretchable and expandable material being capable of readily expanding to provide a greater volume and readily returnable to its original configuration, said receiving means having the edges thereof reinforced by a substantially flat planar thickening of the periphery of said stretchable and expandable material to form a reinforced edge;

an attaching means, said attaching means being applied to the surface on one side of said receiving means at the outer peripheral edges thereof for attaching said female catheter to a female patient; and a drainage means, said drainage means being formed monolithically with said receiving means said drainage means and said receiving means of said female catheter being thereby of one-piece construction.

2. The female catheter as recited in claim 1, wherein said attaching means for attaching said female catheter to a patient are adhesive means, said adhesive means being applied to the substantially flat thickening of the material forming the reinforced edge.

3. The female catheter as recited in claim 5, and additionally a storage means, said drainage means being connected to said storage means said storage means consisting of:

a transporting element, said transporting element being connected to said drainage means and conducting liquid from said drainage means, said drainage means being located in the lower portion of said receiving means;

a storage container, said storage container being connected to said transporting element and storing liquid received from said transporting element; and a securing element, said securing element connected to said storage container to attach said storage container to said patient's leg.

4. The female catheter as recited in claim 1, wherein said female catheter may be flushed, for purposes of cleaning and sanitizing, through said drainage means, while in place on a patient.

5. The female catheter as recited in claim 1, wherein said substantially flat receiving means has a first end portion, a second end portion, and a third portion, said third portion being located between said first and second end portions, said first end portion being wider than said second end portion, said first end portion being arc-like across the end thereof, said second end portion being point-like across the end thereof, said point-like end being rounded, said third portion being narrower than said first end portion and wider than said second end portion, said third portion being of a substantially elongated thickened "T" configuration with the thickened "T" end nearer to said first end portion, said structure of said receiving means tapering in configurartion from said third portion to the extreme lateral ends of said first and said second end portions, said substantially flat and elongated receiving means completely surrounding and covering the vulva area of the female patient and avoiding covering the anus of the female patient when attached to the body of the female patient.

* * * * *

UNITED STATES PATENT AND TRADEMARK OFFICE
CERTIFICATE OF CORRECTION

PATENT NO. : 4,233,978
DATED : November 18, 1980
INVENTOR(S) : Glen A. Hickey

It is certified that error appears in the above—identified patent and that said Letters Patent is hereby corrected as shown below:

In the specification:

Column 2, line 64, "it's" should read --its--;

Column 3, line 13, "rubberlike" should read --rubber-like--;

In the claims:

Claim 1, column 4, line 55, cancel "(as recited in claim 4, wherein)";

Claim 3, column 5, line 21, "claim 5" should read --claim 1--.

Signed and Sealed this

Twenty-first Day of April 1981

[SEAL]

Attest:

RENE D. TEGTMEYER

Attesting Officer    Acting Commissioner of Patents and Trademarks